United States Patent
Butler et al.

(10) Patent No.: US 7,572,945 B2
(45) Date of Patent: Aug. 11, 2009

(54) TOLUENE DISPROPORTIONATION CATALYST

(75) Inventors: James R. Butler, League City, TX (US); Xin Xiao, Houston, TX (US); Rosa Hall, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 11/820,230

(22) Filed: Jun. 19, 2007

(65) Prior Publication Data

US 2008/0319243 A1  Dec. 25, 2008

(51) Int. Cl.
    *C07C 6/12* (2006.01)
(52) U.S. Cl. ...................................... 585/475
(58) Field of Classification Search ............... 585/475
     See application file for complete search history.

(56) References Cited

U.S. PATENT DOCUMENTS

| | | | |
|---|---|---|---|
| 3,808,284 A * | 4/1974 | Wallace et al. ............. 585/475 | |
| 4,665,258 A | 5/1987 | Butler et al. | |
| 4,723,049 A | 2/1988 | Menard et al. | |
| 4,761,514 A | 8/1988 | Menard et al. | |
| 4,956,511 A | 9/1990 | Butler et al. | |
| 6,462,247 B1 | 10/2002 | Kelly et al. | |
| 6,706,937 B2 | 3/2004 | Xiao et al. | |
| 6,803,493 B1 | 10/2004 | Xiao et al. | |
| 2003/0036670 A1 | 2/2003 | Oh | |
| 2006/0149106 A1 | 7/2006 | Xiao et al. | |

* cited by examiner

*Primary Examiner*—Thuan Dinh Dang
(74) *Attorney, Agent, or Firm*—Tenley R. Krueger

(57) ABSTRACT

A process for the disproportionation of a toluene containing feedstock employing a nickel modified mordenite catalyst comprising particulate mordenite having nickel dispersed throughout the catalyst particles to provide surface nickel and interior nickel within the mordenite crystal structure. The catalyst is pretreated to selectively deactivate the surface nickel to provide a surface nickel content of reduced catalytic activity. The interior nickel thus has a higher catalytic activity than the surface nickel. The feedstock is supplied to a reaction zone containing the catalyst to cause disproportionation of toluene in the feedstock to produce a mixture of benzene and xylene. The non-aromatic content of the product is less than the non-aromatic content of a corresponding disproportionation product which would be produced by the disproportionation of the feedstream in the presence of a corresponding nickel mordenite catalyst which has not been pretreated.

12 Claims, 5 Drawing Sheets

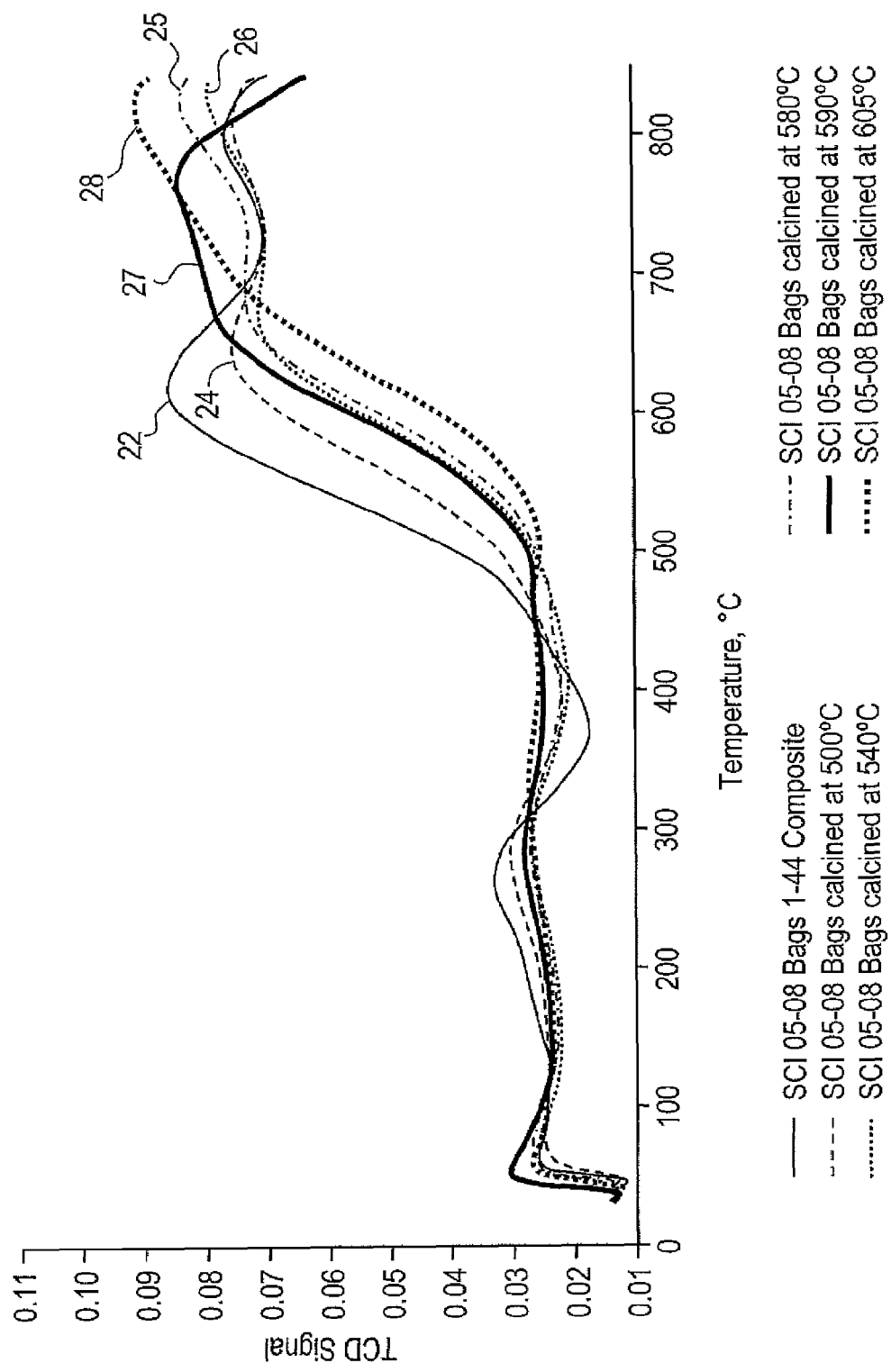

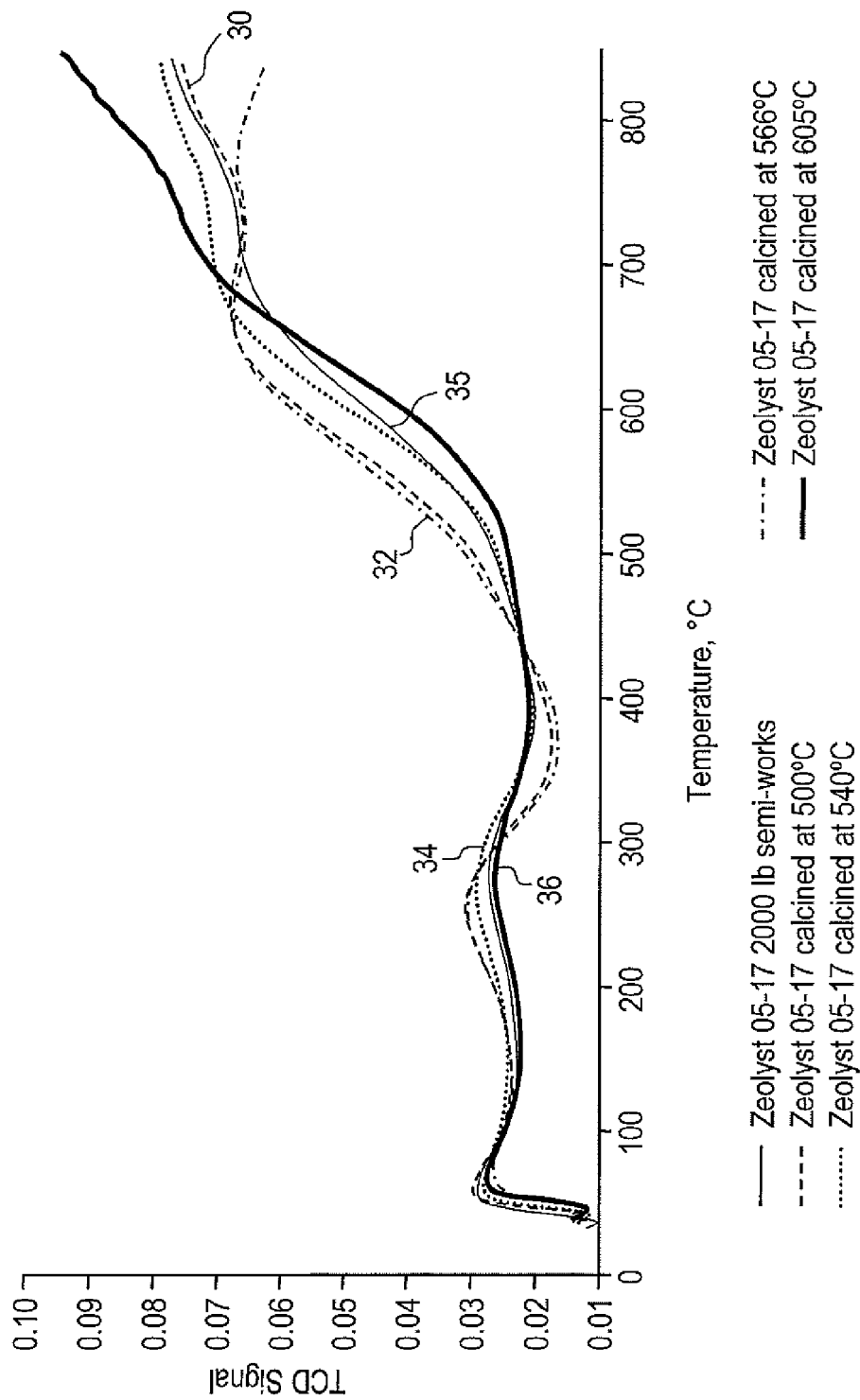

TOLUENE DISPROPORTIONATION CATALYST

FIELD OF THE INVENTION

This invention relates to the treatment of nickel modified mordenite catalysts and the disproportionation of toluene employing nickel modified mordenite catalysts.

BACKGROUND OF THE INVENTION

Mordenite is one of a number of catalysts commonly employed in the transalkylation of alkyl aromatic compounds. Mordenite is a crystalline alumino silicate zeolite having a network of silicon and aluminum atoms interlinked in its crystalline structure through oxygen atoms. For a general description of mordenite catalysts, reference is made to Kirk-Othmer Encyclopedia of Chemical Technology, $3^{rd}$ Edition, 1981, under the heading "Molecular Sieves", Vol. 15, pages 638-643. Mordenite, as found in nature or as synthesized, typically has relatively low silica to alumina mole ratio of about 10 or less. Such conventionally structured mordenite catalysts can be employed in the disproportionation of toluene. However, mordenite catalysts having a substantially lower alumina content can also be employed in the disproportionation of toluene.

Hydrogen, along with toluene, may be supplied to the reactor in which the toluene disproportionation reaction is carried out. While the disproportionation of toluene to benzene and xylene has no net change in hydrogen, a hydrogen co-feed or input may be employed in order to prolong the useful life of the catalyst. In addition to the benzene and mixed xylenes content of the feedstock, non-aromatic compounds may also be formed as a side reaction. Even relatively low non-aromatic levels of about 1-2 wt. % can lead to rapid catalyst deactivation and thus should usually be avoided.

Mordenite modified by the inclusion of a metallic component such as nickel can be employed in the disproportionation of toluene containing feedstocks. The disproportionation of toluene feedstocks may be carried out at temperatures ranging from about 200° to about 600° C. or above and at pressures ranging from about atmospheric to about 100 atmospheres or above. Operating conditions may vary depending upon process parameters such as space velocity and hydrogen/toluene mole ratio and the silica/alumina ratio of the mordenite catalyst. Where the silica alumina ratio is relatively high, toluene disproportionation reactions may be carried out at somewhat lower temperatures than when the silica alumina ratio is relatively low.

SUMMARY OF THE INVENTION

In accordance with the present invention, there is provided a process for the disproportionation of a toluene containing feedstock employing a nickel modified mordenite catalyst. The invention is carried out with a toluene disproportionation catalyst comprising particulate mordenite in which the mordenite is modified by the inclusion of nickel dispersed throughout the mordenite catalyst particles. The dispersion of nickel on the mordenite particles provides nickel sites on the surface of the catalyst particles and in the interior within the channels of the mordenite crystal structure. The nickel modified mordenite is pretreated to selectively deactivate the nickel on the surface of the catalyst particles, thus providing nickel sites on the surface with reduced catalytic activity. The nickel sites in the interior in the mordenite channels thus have a higher catalytic activity than the nickel sites on the surface.

A feedstock containing toluene and hydrogen is supplied to the reaction zone which is operated under temperature and pressure conditions effective to cause disproportionation of toluene in the feedstock to produce a mixture of benzene and xylene. The product stream recovered from the reaction zone contains xylene and benzene without the presence of non-aromatics or with a very low non-aromatic content. The non-aromatic content of the product is a value less than the non-aromatic content of a corresponding toluene disproportionation product which would be produced by the disproportionation of the mordenite feed stream in the presence of a corresponding nickel mordenite catalyst which is similar to the pretreated catalyst but which has not been pretreated. Non-aromatic species are undesired byproducts whose relative amounts are dependent upon the properties of the catalyst. The non-aromatic byproduct concentrations for the improved catalysts of this invention are low and between 0 and 1% selectively at steady state reactor performance.

In a further aspect of the invention, there is provided a method for the treatment of a mordenite disproportionation catalyst. In this embodiment of the invention, there is provided a nickel modified mordenite disproportionation catalyst as a starting material. Typical nickel mordenite catalysts can be characterized by temperature programmed reduction (TPR) using a thermoconductivity detector (TCD) to detect the surface nickel sites and the interior nickel sites. The surface nickel sites are reduced at a lower temperature than the interior nickel sites by TPR analysis. This low temperature TPR peak for the surface nickel sites is in the region of about 200°-300° C. The nickel modified mordenite toluene disproportionation catalyst is calcined at a temperature and for a time sufficient to provide a TPR profile exhibiting a TCD signal characteristic of nickel which has a low temperature TPR peak with an amplitude that is less than the amplitude corresponding to the early nickel peak of the catalyst prior to calcination. This early nickel TCD peak after calcination occurs at a temperature greater than the early nickel TCD peak of the catalyst prior to calcination. In one embodiment of the invention, the catalyst is calcined at a temperature of at least 550° C. and more specifically 575-625° C. In an aspect of the invention, the catalyst is calcined at the temperature within the range of 525-625° C. for a period of at least 0.5 hours. In another aspect of the invention, the catalyst is calcined at a temperature within the range of 525° C.-625° C. for a period of up to 24 hours.

In a further aspect of the invention, there is provided a method for the disproportionation of a toluene containing feedstock employing a nickel modified mordenite catalyst which has been calcined at a temperature of at least 525° C. to provide a TPR profile as described above. Toluene containing feedstocks and hydrogen are supplied to the reaction zone containing the calcined nickel modified mordenite catalyst to generate a product stream containing xylene and benzene with a low non-aromatic hydrocarbon content as described previously. In an embodiment, the non-aromatic content of the product is a value less than the non-aromatic content of a corresponding toluene disproportionation product produced in the presence of nickel mordenite catalyst corresponding to the catalyst but without calcination in order to reduce the early nickel peak of the catalyst. In a further embodiment, the non-aromatic byproduct concentrations for the improved catalysts of this invention are between 0 and 1% selectivity at a steady state reactor performance i.e., when the reactor after startup reaches steady state conditions of temperature, pressure and space velocity.

In one aspect of the invention, the toluene containing feedstock is supplied to the reaction zone to provide a liquid hourly space velocity (LHSV) within the range of 1.5-4.5 hrs$^{-1}$. The reaction zone is operated at a temperature within the range of 300-450° C. at an average pressure within the range of 30-65 bar. In a further embodiment of the invention, the calcined nickel modified mordenite catalyst has an active surface nickel content after calcination which is less than the active surface nickel content of the nickel modified mordenite catalyst prior to calcination. In another embodiment of the invention, the nickel modified mordenite catalyst is sulfided to provide a sulfur content of at least 20 mole % relative to the nickel content. The nickel modified mordenite catalyst is sulfided prior to being calcined. Different procedures for sulfiding the catalyst can be used. In an embodiment, the catalyst is sulfided as described in Publication No. US2006/0149109 (published Jul. 6, 2006) of U.S. application Ser. No. 11/030,707 to Xiao et al., filed on Jan. 6, 2005, and entitled "Toluene Disproportionation Process Utilizing Mild Sulfiding During Startup"; the entire disclosure of which is incorporated herein by reference.

In a further embodiment of the invention, the hydrogen is supplied to the reaction zone in an amount to provide a hydrogen/hydrocarbon mol ratio of at least 1. In another embodiment of the invention, the hydrogen is supplied to the reaction zone in an amount to provide a hydrogen/hydrocarbon mole ratio of 3:1. The hydrogen may be supplied to the reaction zone in stages in which the amount of hydrogen supplied to the reaction zone is increased to provide a later hydrogen/hydrocarbon mole ratio which is greater than the initial hydrogen to hydrocarbon mole ratio. In this aspect of the invention, the hydrogen may be added to the reaction zone to provide hydrogen/hydrocarbon mole ratio of at least 3:1 up to about 5:1 at an interval after the initial start of the disproportionation reaction until the amount of non-aromatics is less than 1%.

BRIEF DESCRIPTION OF THE DRAWINGS

FIG. 4 is a graph of a TPR data for a nickel modified mordenite catalyst depicted in FIG. 2 at progressively increasing calcination temperature.

FIG. 5 is a graph of a TPR data for a nickel modified mordenite catalyst depicted in FIG. 3 at progressively increasing calcination temperature.

DETAILED DESCRIPTION OF THE INVENTION

Figure 1:
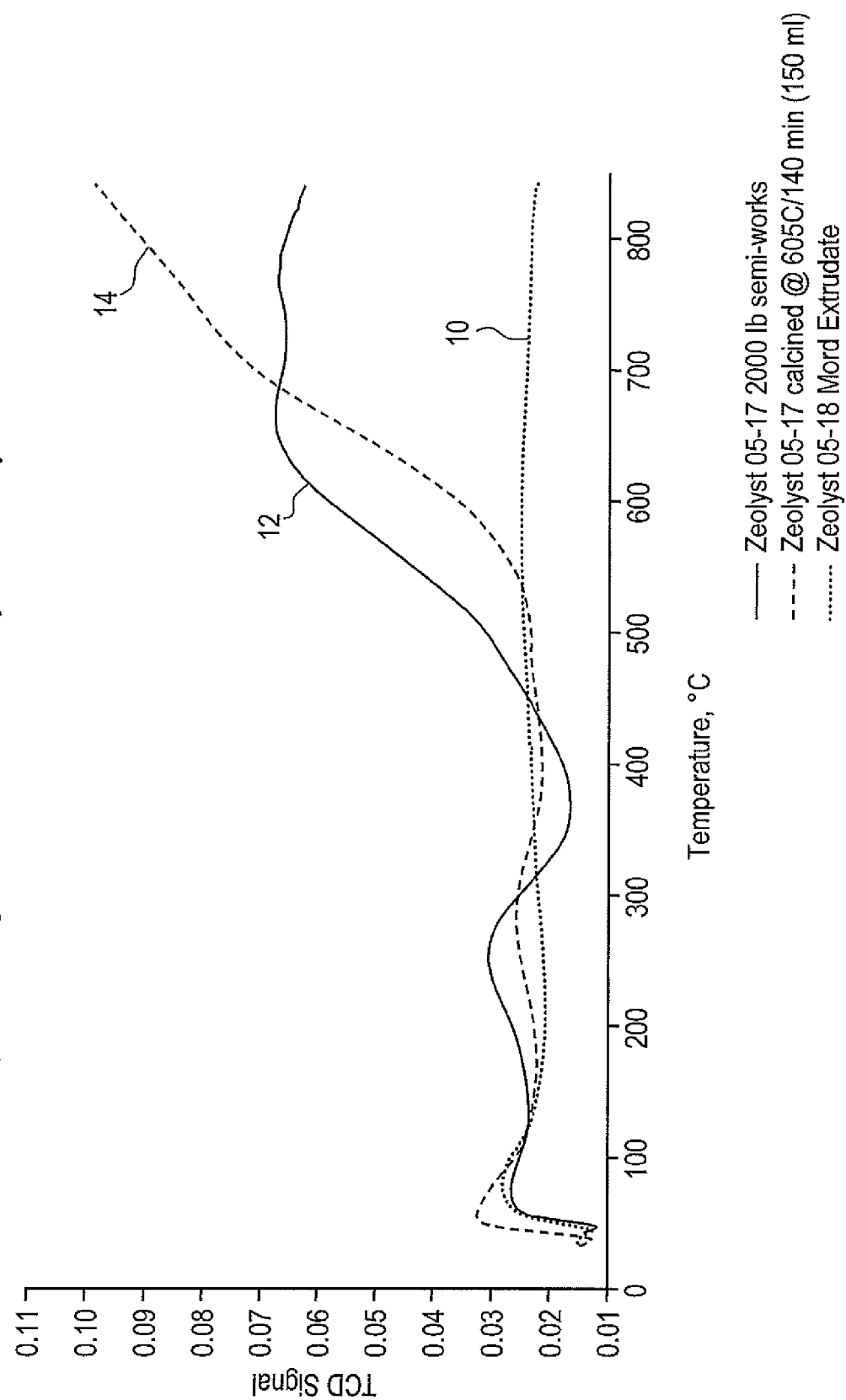
FIG. 1 is a graph illustrating temperature program reduction (TPR) of a nickel modified mordenite catalyst with and without calcination in comparison with mordenite extrudate which has not been modified.

Toluene disproportionation processes can be carried out employing nickel mordenite catalyst to produce a mixture of benzene and xylenes in accordance with the following reaction.

2 Toluene→Benzene+Xylene (1)

The toluene disproportionation reaction is mildly exothermic and results in a product comprising equal molar ratios of benzene and xylene in a product stream comprising benzene and xylenes. The xylenes in the product exhibit relatively high boiling temperatures ranging from about 138°-139° C. for m-xylene and p-xylene to about 144° C. for o-xylene. The benzene in the product stream, of course, exhibits a substantially lower boiling point of about 80° C. which is substantially less than the boiling point of the feedstock toluene of about 118° C. In addition to the reaction product containing a mixture of benzene and xylenes as described above, the reaction product also contains a relatively low content of non-aromatic hydrocarbons.

The disportionation of toluene feed stocks may be carried out at temperatures ranging from about 300-450° C. and at pressures ranging from 35-65 bars or even higher. As described in U.S. Pat. Nos. 4,665,258 and 4,956,511 to Butler et al, mordenite catalysts may be promoted by the inclusion of nickel in amounts ranging from 0.5-10% of the mordenite. The nickel may be incorporated into the mordenite by ion exchange or impregnation techniques as described in the aforementioned U.S. Pat. Nos. 4,665,258 and 4,956,511, the entire disclosures of which are incorporated herein by reference. After incorporating nickel into the mordenite crystal structure, the mordenite can by mulled with a suitable binder such as silica or alumina and then extruded to form catalyst particles typically having a diameter of about ⅛-¼".

The nickel modified mordenite catalyst employed in carrying out the present invention can be characterized in terms of a Temperature Program Reduction (TPR) scan. The TPR scan is a well known procedure for evaluating a catalyst. In the TPR procedure the catalyst is subjected to a hydrogen atmosphere and is heated to progressively higher temperatures. As the catalyst sample is heated, thermoconductivty measurements are made employing a thermoconductivity detector (TCD). The TPR and TCD measurements may be carried out employing conventional instruments such as the chemisorption analyzer designates Chem Bet-3000 available from Quantachrome Instruments, Boynton Beach, Fla. In conducting the TPR measurements, the catalyst under investigation is placed in a reaction chamber and a minor amount of hydrogen in an argon carrier is passed over the catalyst as the catalyst is progressively heated. As the catalyst is heated, nickel is reduced and the hydrogen content of the gas issuing from the chamber is lowered correspondingly. As described below with respect to the exemplary catalysts which may be employed in carrying out the invention, the TCD signal is measured to provide an indication of the nickel content of the catalyst as the catalyst is progressively heated. More particularly for a nickel modified mordenite catalyst in which the nickel is disposed both externally and internally within the catalyst particle, as the catalyst is heated, a low temperature TPR peak is detected corresponding to the reduction of nickel at the surface sites of the catalyst particle. Upon continued heating of the catalyst particle, a higher temperature TPR peak is observed that corresponds to the interior nickel sites in the channels of the mordenite crystallite. The majority of the nickel is in the mordenite channels.

In carrying out the present invention, pretreatment of the nickel modified mordenite catalyst to reduce the catalytic activity of the surface nickel provides for a reduction in the non-aromatic hydrocarbon content of the product from the toluene disportionation reactor. Selective deactivation of the surface nickel of the mordenite catalyst particles can be accomplished by calcining the catalyst particles at a temperature and for a time effective to provide a substantial decrease in the early nickel peak observed during TPR analysis of the catalyst.

In experimental work respective of the invention, TPR analysis of a mordenite toluene disportionation catalyst was carried out on the three catalyst samples of a commercially available mordenite catalyst, identified here as Catalyst A. In one case, the catalyst was formed with a binder and extruded to produce an extrudate sample without nickel modification. In another case, an extrudate of the catalyst incorporating nickel in an amount of 0.5-1.5 wt. % relative to the mordenite was employed. This nickel modified mordenite catalyst was subjected to TPR analysis without calcination and after calcination at 605° C. for more than 30 minutes. The calcination was carried out on a 150 cc sample.

of 0.8, 3.8 and 4.8 days. The feed used was toluene at a nominal liquid hourly space velocity (LHSV) of 1-4.5 hr$^{-1}$ with a hydrogen to hydrocarbon molar ratio at a startup of 1:1. The temperature was adjusted to hold a constant conversion and the inlet pressure was between 30-65 bars. The target conversion was 47+/−1 wt. % corresponding to 53 wt. % toluene in the effluent. The catalyst volume in the reactor was 30 cc of 14-20 mesh catalyst. As can be seen from the results shown in Table 1, the non-aromatics concentration dropped to low levels below 1% very rapidly. Thus, at the first entry at 0.8 days the liquid non-aromatics content was only 0.7% and remained at an even lower value of 0.5% afterwards. Similar toluene disportionation laboratory work for the non-calcined catalyst showed that the typical disportionation experiment did not achieve less than 1% liquid non-aromatics as quickly during startup of the run and can be from 2-6 days.

TABLE 1

Test Conditions and Results For Catalyst A Calcined at 605° C.

| TOS | Temp. | Press. | LHSV | H2/tol | Conv. | Selectivities, wt % | | | | | Liquid |
|---|---|---|---|---|---|---|---|---|---|---|---|
| days | ° F. | psig | hr$^{-1}$ | (molar) | wt % | n-Ar | EB | BZ | XYL | HVY | n-Ar |
| 0.8 | 659 | 598 | 3.0 | 1.0 | 41.6 | 0.8 | 0.4 | 41.9 | 47.3 | 9.6 | 0.7 |
| 3.8 | 677 | 598 | 3.1 | 1.0 | 43.9 | 1.1 | 0.4 | 41.1 | 45.9 | 11.5 | 0.5 |
| 4.8 | 686 | 598 | 3.1 | 1.0 | 47.8 | 0.7 | 0.5 | 40.6 | 44.4 | 13.9 | 0.5 |

The results of the comparative TPR analysis of the three mordenite catalyst samples are illustrated in FIG. 1 in which the amplitude of the TCD signal is plotted on the ordinate versus the temperature on the abscissa. In FIG. 1, curve 10 is plot of the TCD signal for the catalyst extrudate without modification by nickel. Curve 12 is a graph of the TCD signal for the extruded nickel modified mordenite catalyst without the additional calcination and Curve 14 is a graph of the TCD signal after calcination at 605° C. as described above. As can be seen by an examination of FIG. 1, Curve 10 is relatively flat throughout the temperature scan after startup, indicating the absence of nickel. Curve 12 for the uncalcined nickel modified catalyst shows a pronounced low temperature nickel peak at about 260° C. indicative of surface nickel on the mordenite catalyst. A second high temperature nickel peak indicative of interior nickel starts at about 500° C. and reaches a peak at about 660° C.

The TPR analysis of the nickel modified mordenite after calcination, as indicated by Curve 14, shows that the low temperature nickel peak was reduced to a near minimum value and was also shifted to a temperature of about 300° C. The high temperature nickel peak was also shifted to the right to a temperature above 800° C. In considering the data shown in FIG. 1, it should be recognized that the low temperature nickel peak at 260° C. for the catalyst without calcination indicates the presence of easily reducible surface nickel. This easily reducible nickel in the catalyst is undesirable in the toluene disportionation process since it results in an enhanced non-aromatics content of the product and an exotherm during startup of the disportionation process.

The calcined catalyst was employed in a laboratory toluene disportionation reactor carried out under test conditions set forth in Table 1 with analysis made at time on stream (TOS)

Figure 2:
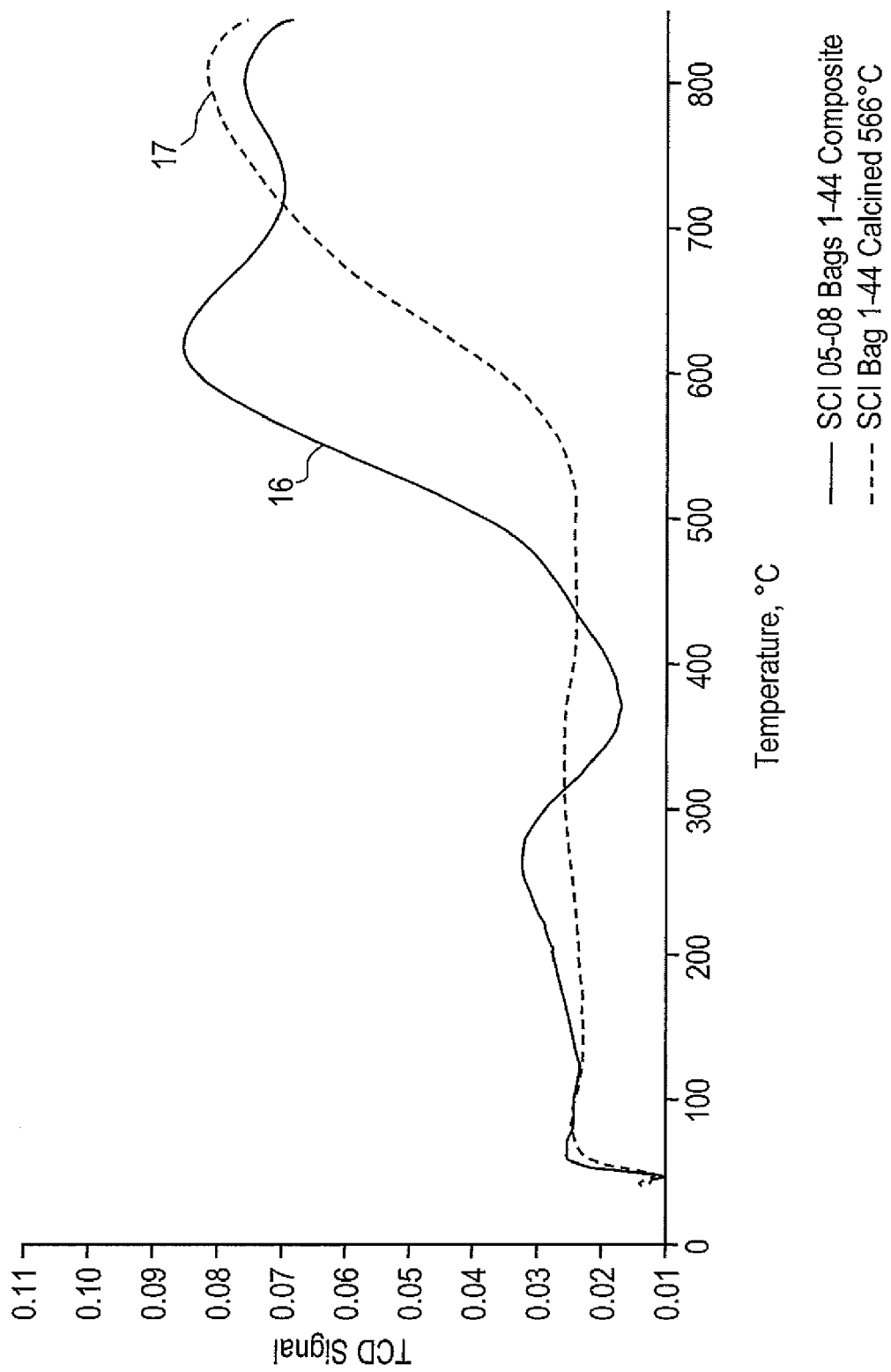
FIG. 2 is a graph showing TPR data for a nickel modified mordenite catalyst with and without calcination.

A second nickel modified mordenite catalyst (Catalyst B) was subjected to a TPR analysis before and after calcination. In this case, the catalyst was calcined at 566° C. for two hours. The results of the TPR analysis are illustrated in FIG. 2 in which curve 16 is a graph of the TCD signal plotted on the ordinate versus the temperature on the abscissa for the non-calcined catalyst. Curve 17 shows a corresponding plot for the calcined catalyst. The results here are very similar to the results depicted in FIG. 1 for the catalyst identified as Catalyst A. Again, the early nickel peak was nearly eliminated and was shifted from about 260° C. for the uncalcined catalyst to about 300-350° C. for the calcined catalyst. The high temperature peak corresponding to interior nickel was shifted to a higher temperature region similarly as for the Catalyst A depicted in FIG. 1.

This calcined catalyst was then employed in a toluene disportionation reactor employing the same reactor and conditions described above for Catalyst A. The feed was toluene at a nominal space velocity of LHSV of between 1-3.5 hr$^{-1}$ with a hydrogen to hydrocarbon molar ratio at a startup of 1:1. The temperature was adjusted to hold a constant conversion and the inlet pressure was 30-65 bar. The target conversion was 47+/−1 corresponding to 53 wt. % toluene in the effluent. The catalyst volume in the reactor was between 10-50 cc of 14-20 mesh catalyst.

In this toluene disportionation run, the calcined catalyst was subject to a mild sulfiding at the start up of the procedure. Sulfiding was accomplished using dimethyldisulfide to provide at least 20 mole % sulfur relative to the nickel in the catalyst. The results of this test run over a time of about 8 days after startup are shown in Table 2. As indicated the non-aromatics content was acceptable throughout the test run.

TABLE 2

Test Conditions and Results for Catalyst B Calcined at 566° C.

| TOS | Temp. | Press. | LHSV | H2/tol | Conv | Selectivity, wt % | | | | | Liquid |
|-----|-------|--------|------|--------|------|------|-----|------|------|-----|--------|
| days | ° F. | psig | hr-1 | (molar) | wt % | n-Ar | EB | BZ | XYL | HVY | n-Ar |
| 0.9 | 653 | 596 | 3.0 | 1.0 | 33.9 | 2.2 | 0.3 | 41.6 | 48.5 | 7.4 | 0.7 |
| 2.1 | 671 | 596 | 3.0 | 1.0 | 39.3 | 3.3 | 0.4 | 41.3 | 47.2 | 7.9 | 0.5 |
| 3.9 | 689 | 596 | 3.0 | 1.0 | 45.2 | 1.1 | 0.5 | 42.4 | 46.9 | 9.1 | 0.8 |
| 4.9 | 700 | 596 | 3.0 | 1.0 | 47.5 | 0.8 | 0.5 | 42.7 | 46.7 | 9.3 | 0.6 |
| 5.9 | 702 | 446 | 3.0 | 1.0 | 46.8 | 0.8 | 0.5 | 42.5 | 47.0 | 9.3 | 0.6 |
| 6.9 | 706 | 596 | 3.0 | 1.0 | 47.3 | 0.9 | 0.5 | 42.6 | 46.6 | 9.4 | 0.6 |
| 7.9 | 709 | 596 | 3.0 | 1.0 | 47.8 | 0.8 | 0.5 | 42.6 | 46.5 | 9.6 | 0.6 |

Figure 3:
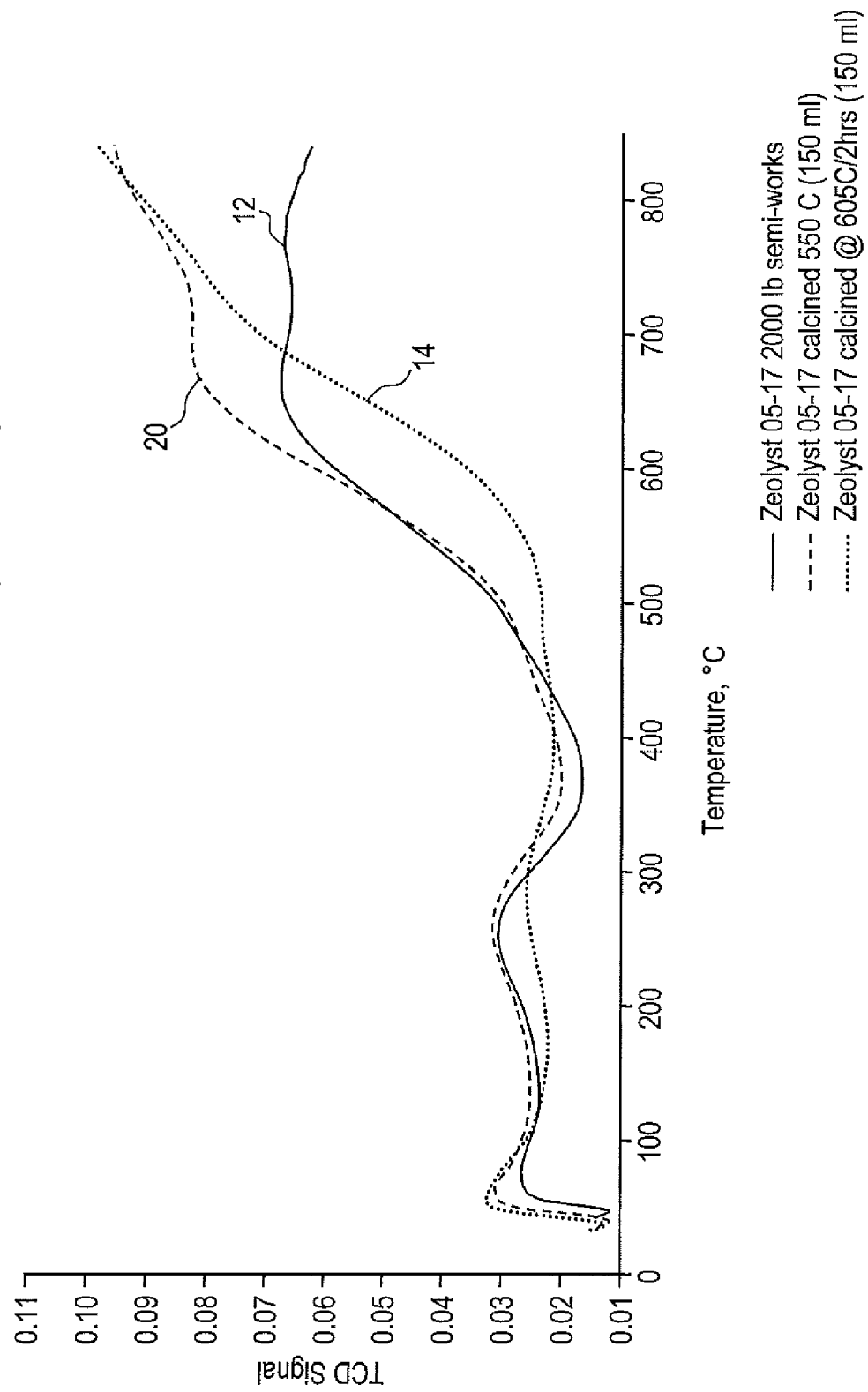
FIG. 3 is a graph illustrating TPR data for a nickel mordenite catalyst with and without calcination at two different temperatures.

Additional experimental work was carried out employing the nickel modified mordenite (Catalyst A) with calcination at 550° C. This contrasted with the calcination at 605° C. as shown in FIG. 1. The TPR analysis of this catalyst is illustrated in FIG. 3 in which Curve 20 indicates the TPR results for the catalyst calcined at 550° C. Curves 12 and 14 of FIG. 3 are reproduced from FIG. 1 and respectively show the results for the uncalcined catalyst and the catalyst calcined at 605° C. As indicated by the curves shown in FIG. 3 for Catalyst A, the desired minimum calcination temperature should be at least 550° C. ranging up to the 605° C. level employed previously.

Further experimental work was carried out employing Catalyst B calcined at temperatures ranging from 500° C. to 605° C. The Catalyst B samples were calcined at temperatures ranging from 500-605° C. for two hours. The calcined samples were then analyzed to obtain TPR curves for the catalyst samples calcined at 500° C., 540° C., 580° C., 590° C. and 605° C. The results of this work are illustrated in FIG. 4, which is a graph of the TCD amplitude plotted on the ordinate versus temperature on the abscissa. In FIG. 4 the TPR curve for the uncalcined catalyst is indicated by the Curve 22. The results for samples calcined at 500° C., 540° C., 580° C., 590° C., and 605° C. are illustrated by Curves 24, 25, 26, 27 and 28 respectively. As can be seen from an examination of FIG. 4 the uncalcined sample illustrated by Curve 22 showed a very pronounced low temperature nickel peak at 270° C. Curve 24 indicates the results for calcination at 500° C. and shows a flattening of the low temperature nickel peak but the peak still had significant amplitude. The early nickel peaks for Curves 25, 26 and 27 corresponding to calcination temperatures of 540° C., 580° C., and 590° C. respectively are shown in FIG. 4 to be largely overlapped but exhibit significant flattening of the low temperature nickel peak with a shift to a somewhat higher temperature. Curve 28, corresponding to the sample calcined at 605° C., showed very significant flattening of the early nickel peak with the peak shifting to above 300° C.

The catalyst samples were analyzed for BET surface area and porosity characteristics with results indicated that the samples were not damaged during calcinations. The sample calcined at the highest temperature, 605° C., still maintained over 93% surface area relative to the surface area of the uncalcined sample. Small decreases in pore diameter and pore volume were also observed in correlation with the decrease in surface area because of the collapse of small pores into larger pores. The surface area, pore volume and pore size for the uncalcined and calcined samples are shown below in Table 3.

TABLE 3

Surface Area, Pore Volume and Pore Size (Pt Dispersion) of Catalyst B

| Catalyst | SA, m²/g | PV, cm³/g | PD, Å |
|----------|----------|-----------|-------|
| Reference | 370 | 0.40 | 43 |
| Calcined at 500° C. | 359 | 0.48 | 53 |
| Calcined at 540° C. | 371 | 0.41 | 44 |
| Calcined at 580° C. | 350 | 0.43 | 49 |
| Calcined at 590° C. | 345 | 0.41 | 48 |
| Calcined at 605° C. | 347 | 0.43 | 49 |

A similar stepwise calcination analysis for Catalyst A was carried out for samples calcined at 500° C., 540° C., 566° C. and 605° C. The TPR curves for these catalyst samples are shown in FIG. 5 in which the TDC signal is plotted on the ordinate versus temperature in ° C. on the abscissa. Curve 30 for the uncalcined sample, and Curve 32 for the sample calcined at 500° C. largely overlap one another both at the early nickel peak as well as the later peak indicative of interior nickel. Curve 34, indicating the results for the catalyst calcined at 540° C., shows only a moderate flattening of the low temperature nickel peak whereas Curves 35 and 36 corresponding to calcination temperatures of 566° C. and 605° C., respectively show a substantial flattening of the low temperature nickel peak.

The surface area, pore volume and pore diameter analysis of the uncalcined and calcined samples of Catalyst A are illustrated in Table 4. The analysis here, similarly as with the analysis described previously for Catalyst B, showed little or no damage to the catalyst as the result of the high temperature calcination procedures.

TABLE 4

Surface Area, Pore Volume and Pore Size (Pt Dispersion) of Catalyst A.

| Catalyst | SA, m²/g | PV, cm³/g | PD, Å |
|----------|----------|-----------|-------|
| Reference | 374 | 0.37 | 39 |
| Calcined at 500° C. | 357 | 0.46 | 52 |
| Calcined at 540° C. | 348 | 0.41 | 48 |
| Calcined at 566° C. | 358 | 0.37 | 42 |
| Calcined at 605° C. | 350 | 0.40 | 46 |

The foregoing experimental work shows that a flattening of the low temperature TPR peak is indicative of deactivation of surface nickel which can be achieved through high temperature calcination and also results in a low non-aromatic hydrocarbon content. For the commercial catalyst, identified as Catalyst B, calcination temperatures ranging from 540° C.-605° C. showed substantial flattening of the low temperature nickel peak while still maintaining satisfactory catalyst characteristics in terms of surface area, pore volume and pore size compared to the reference catalyst without calcination. For Catalyst A, while acceptable catalyst characteristics in terms of surface area, pore volume and pore size were reported across the range of calcination temperatures, substantial flattening of the early nickel peak occurred at calcination temperatures of 566° C. and 605° C. At a lower calcination temperature of 540° C., the early nickel peak, as indicated by TPR analysis, remained prominent.

As described previously, the treatment of nickel modified mordenation catalyst to selectively deactivate nickel on the surface of the catalyst particles enables toluene disportionation to be carried out with exceptionally low non-aromatics content in the product recovered from the disportionation reactor. Such surface nickel deactivation can be accomplished by calcinating the nickel modified catalyst at temperatures sufficient to materially decrease the early nickel peak characterized in the region of 200-300° C. as indicated by the TPR profile of the catalyst. The reduction in the maximum temperature of the early nickel peak is accomplished by a slight shift in the peak to a moderately higher temperature than that observed for the original catalyst prior to calcination. For the catalysts investigated, calcination may be carried out at temperatures ranging up to 605° C. providing acceptable surface area pore volume and pore size characteristic of the catalyst. Calcination can be carried out at the foregoing temperatures at times ranging from about ¼ an hour to 3 hours to arrive at a desired pretreatment level. In the calcination procedure, the catalyst can be heated rapidly or gradually while still retaining acceptable results. The catalyst acid sites are not adversely affected by calcination under the conditions employed in carrying out the present invention as demonstrated by the extent of the disproportion reactions observed. Also ammonia temperature programmed desorption (TPD) analysis carried out on the foregoing catalyst samples identified as Catalyst A and Catalyst B, before and after calcination shows that the acid site density and strength distribution exhibit little difference between the non-calcined and the calcined catalyst. Percent ammonia desorption for the various catalyst examples reached values of about 5% ammonia +/−1% with a maximum amplitude at about 250-300° C. The results show that the catalyst samples were improved with respect to the nickel sites without compromising the acid sites during calcination.

The nickel modified mordenite catalyst may be advantageously subjected to sulfiding although sulfiding is not necessary in order to achieve the desirable modification of surface nickel in accordance with the invention. However, the combination of sulfiding and calcination shows improved results as indicated by the experimental work set forth in Table 2. For the same catalyst, Catalyst B, without sulfiding, calcination at 566° C. for 2 hours resulted in a catalyst which exhibited higher liquid non-aromatics content immediately after startup. However, after 5 days on stream, the liquid aromatics content evened out to a value of less than 1 wt. %. Where sulfiding is employed, the catalyst is desirably sulfided after calcination to provide a sulfur content relative to nickel of at least 20 mole %.

Hydrogen can be co-fed along with toluene to the disportionation reactor in amounts normally employed for non-treated nickel mordenite catalyst. Typically the hydrogen is supplied initially at a relatively low value, a hydrogen to hydrocarbon mole ratio for about 1 or more, and there after increased to a higher value to provide a hydrogen hydrocarbon mole ratio of about 3:1 or above. This increase in the hydrogen to hydrocarbon mole ratio may be accomplished more rapidly within no more than 6 days after the start of the disportionation reaction.

Having described specific embodiments of the present invention, it will be understood that modifications thereof may be suggested to those skilled in the art, and it is intended to cover all such modifications as fall within the scope of the appended claims.

The invention claimed is:

1. A method for the disproportionation of a toluene containing feedstock comprising:
   a) providing a reaction zone containing a nickel modified mordenite type toluene disproportionation catalyst which has been calcined at a temperature of from about 566° C. to about 605° C. for a time of from about 30 minutes to about 2 hours to provide a TPR profile exhibiting a TCD signal having low temperature nickel peak of an amplitude which is less than the amplitude of the corresponding low temperature nickel peak of a corresponding nickel-modified mordenite catalyst without calcination and wherein said nickel modified mordenite catalyst has an active surface nickel content after calcination which is less than the active surface nickel content of the nickel modified mordenite catalyst prior to calcination;
   b) supplying a toluene containing feedstock and hydrogen to said reaction zone;
   c) operating said reaction zone under temperature and pressure conditions effective to cause the disproportionation of toluene in said feedstock in the presence of hydrogen to benzene and xylene; and
   d) recovering a product stream from said reaction zone containing xylene and benzene and having a non-aromatics content less than the non-aromatic content of a corresponding toluene disproportionation product produced by the disproportionation of said toluene containing feed stream in the presence of a nickel mordenite catalyst corresponding to said calcined catalyst but without calcination.

2. The method of claim 1 wherein said toluene containing feed stock is supplied to said reaction zone in an amount effective to provide a LHSV within the range of 1 to 4.5 hrs⁻.

3. The method of claim 2 wherein said reaction zone is operated at a temperature within the range of 300-450° C. at an average pressure within the range of 30-45 bar.

4. The method of claim 1 wherein said hydrogen is supplied to said reaction zone in an amount to provide a mole ratio of hydrocarbon of at least 1.

5. The method of claim 4 wherein said hydrogen is added to said reaction zone in an amount to provide a hydrogen to hydrocarbon mole ratio of at least 3:1 at a time interval after the start of the disportionation reaction of no more than 6 days.

6. The method of claim 1 wherein said nickel modified mordenite catalyst is sulfided to provide a sulfur content of at least 20 mole % relative to the nickel content.

7. The method of claim 6 wherein said nickel modified mordenite catalyst is sulfided after being calcined.

8. A method for the disproportionation of a toluene containing feed stock comprising:
   a) providing a toluene disproportionation catalyst comprising particulate mordenite particles modified by the inclusion of nickel dispersed throughout the mordenite particles to provide surface nickel on the surface of said catalyst particles and interior nickel within the interior of said catalyst particles;

b) pretreating said nickel modified mordenite catalyst particles to selectively deactivate the nickel on the surface of said catalyst particles to provide a nickel content on said surface of reduced catalytic activity whereby the nickel in the interior of said catalyst particles has a higher catalytic activity than the nickel on the surface of said catalyst particles, wherein the pretreatment occurs at a temperature from about 566° C. to about 605° C. for a time of from about 30 minutes to about 2 hours;

c) supplying a toluene containing feedstock and hydrogen to a reaction zone containing the pretreated catalyst particles;

d) operating said reaction zone under temperature and pressure conditions effective to cause the disproportionation of toluene in said feedstock in the presence of hydrogen to benzene and xylene; and e) recovering a product stream from said reaction zone containing xylene and benzene and having a non-aromatics content ranging from 0 to a value less than the non-aromatic content of a corresponding toluene disproportionation product produced by the disproportionation of said toluene containing feedstock in the presence of said nickel mordenite catalyst without pretreatment.

9. The method of claim 8 wherein said toluene disportionation catalyst has a nickel content within the range 0.5-2 wt. % based upon the mordenite in said catalyst.

10. The method of claim 9 wherein said nickel modified mordenite catalyst is sulfided to provide a sulfur content of at least 20 mole % relative to the nickel content.

11. The method of claim 10 wherein said nickel modified mordenite catalyst is sultided after pretreating said nickel modified mordenite catalyst.

12. The method of claim 8 wherein said hydrogen is applied to said reaction zone initially at a low level relative to the toluene supplied said reaction zone and thereafter increasing said hydrogen to provide a greater hydrogen content relative to the toluene supplied to said reaction zone.

* * * * *